(12) United States Patent
Traneus

(10) Patent No.: US 11,213,696 B2
(45) Date of Patent: Jan. 4, 2022

(54) METHOD, SYSTEM AND COMPUTER PROGRAM PRODUCT FOR ION RADIOTHERAPY

(71) Applicant: RaySearch Laboratories AB, Stockholm (SE)

(72) Inventor: Erik Traneus, Uppsala (SE)

(73) Assignee: RaySearch Laboratories AB, Stockholm (SE)

( * ) Notice: Subject to any disclaimer, the term of this patent is extended or adjusted under 35 U.S.C. 154(b) by 193 days.

(21) Appl. No.: 16/599,546

(22) Filed: Oct. 11, 2019

(65) Prior Publication Data

US 2020/0086142 A1    Mar. 19, 2020

Related U.S. Application Data

(63) Continuation of application No. PCT/EP2018/059511, filed on Apr. 13, 2018.

(30) Foreign Application Priority Data

Apr. 13, 2017 (EP) .................................... 17166410

(51) Int. Cl.
*A61N 5/10*    (2006.01)

(52) U.S. Cl.
CPC .... *A61N 5/1031* (2013.01); *A61N 2005/1087* (2013.01)

(58) Field of Classification Search
CPC .... A61N 2005/1087; A61N 2005/1085–1098; A61N 5/10–1084
See application file for complete search history.

(56) References Cited

U.S. PATENT DOCUMENTS

| 5,341,292 A | * | 8/1994 | Zamenhof | G01T 1/2985 600/425 |
| 5,357,429 A | * | 10/1994 | Levy | B33Y 50/00 378/17 |
| 5,381,518 A | * | 1/1995 | Drebin | G06T 17/00 345/421 |
| 2005/0192764 A1 | | 9/2005 | Holland | |
| 2011/0306818 A1 | * | 12/2011 | Bert | A61N 5/1043 600/1 |

(Continued)

FOREIGN PATENT DOCUMENTS

| WO | WO-00/40298 A1 | 7/2000 |
| WO | WO-2013/088336 A1 | 6/2013 |

*Primary Examiner* — Thaddeus B Cox
(74) *Attorney, Agent, or Firm* — Faegre Drinker Biddle & Reath LLP

(57) ABSTRACT

A method of performing dose calculations for ion radiotherapy compensating for tissue in which the density within a voxel may be inhomogeneous by approximating a portion of the voxel as an air cavity. For each dose voxel, the voxel is inscribed in a three-dimensional grid comprising a number of cells and the propagation of ions through the voxel is calculated based on the cell pattern in the at least one cell overlapping the voxel. Preferably, the voxel is inscribed in the three-dimensional grid in such a way that it overlaps at least one cell fully. Each cell comprises a first portion representing a first density corresponding to a density of a tissue and a second portion representing a second density corresponding to the density of air, the first and second portions forming a cell pattern.

13 Claims, 4 Drawing Sheets

(56) References Cited

U.S. PATENT DOCUMENTS

2015/0154374 A1* 6/2015 Hissoiny ................ G16H 50/30
 703/6
2015/0332454 A1* 11/2015 Yin .......................... A61B 6/50
 382/131

* cited by examiner

METHOD, SYSTEM AND COMPUTER PROGRAM PRODUCT FOR ION RADIOTHERAPY

This application is a Continuation Application of International Application No. PCT/EP2018/059511, filed Apr. 13, 2018, and claims benefit of European Patent Application No. 17166410, filed Apr. 13, 2017, the entire contents of which are incorporated by reference herein.

TECHNICAL FIELD

The present invention relates to a method for ion radiotherapy for lung tissue.

BACKGROUND

Radiotherapy using ions such as protons to deposit energy in the patient has a number of advantages.

In ion based radiotherapy each ion will emit most of its energy towards the end of its path, creating what is known as the Bragg peak. A key issue in treatment planning is to ensure that the Bragg peaks of all beams are placed within the treatment volume, in such a way that all parts of the treatment volume receive the prescribed dose while minimizing dose to the surrounding volume.

The position of the Bragg peak is affected by the kinetic energy Tp of each ion. The values for Tp are selected so that the ions having the lowest energy will stop in an area at the nearest end of the treatment volume and the ions having the highest energy will stop in the area at the farthest end of the treatment volume. Therefore, ion based radiotherapy allows the dose to be delivered with a high precision, thus minimizing damage to tissue outside of the volume to be treated.

Tissue having fractal properties, such as lung tissue, poses a particular difficulty, in that it is not homogeneous. Instead, it comprises an irregular pattern of air cavities and tissues with higher densities than air. For example, lung tissue includes an irregular pattern of air cavities called alveoli. The structure of lung tissue affects the trajectory of the ions in ways that causes errors compared to trajectories through homogeneous tissue. Currently used CT imaging systems do not provide sufficiently high resolution to see the individual air cavities. Instead, the CT images will return an average value for the density in the lung tissue.

The air cavities will result in a broadening of the Bragg peaks compared to the case with homogeneous tissue. Using an average value as a basis for ion therapy dose calculations will result in an imprecise modelling of the delivery of the energy.

SUMMARY OF THE INVENTION

It is an object of the present invention to increase the accuracy of radiotherapy dose modelling in lung tissue for ion therapy such as proton radiotherapy.

The invention relates to a method of performing dose calculations for ion radiotherapy, comprising the steps of:
a. for each dose voxel in the volume to be treated that is identified as a fractal tissue voxel, such as a lung dose voxel,
b. inscribing the voxel in a three-dimensional grid comprising a number of cells, preferably in such a way that the voxel overlaps at least one cell fully,
c. wherein each cell comprises a first portion representing a first density corresponding to a density of a tissue and a second portion representing a second density corresponding to the density of air, the first and second portions forming a cell pattern, and
d. calculating the propagation of ions through the voxel based on the cell pattern in the at least one cell overlapping the voxel.

The invention proposes a mathematical approximation of the lung including alveoli, that may be used to calculate the ion propagation through a volume that comprises portions of tissue having a first density and portions of air having substantially zero density. This is superior to using one average density value through the whole volume, since the average value does not account for the variation in density, which affects the ion propagation, as discussed above.

The method proposed by the invention attempts to minimize the uncertainty caused by the alveoli structure. The method involves creating a model of a tissue comprising air cavities, where the relative size of the air cavities within the tissue results in a realistic average density of the model.

The invention enables a representation of the alveoli that is close enough to actual alveoli geometries to yield a satisfactory result in ion radiotherapy treatment planning. Although the shape of the air cavities in the grid will not correspond exactly to the shape and size of the alveoli in an actual lung, the grid structure with inscribed air cavities will model sufficiently accurately the trajectory of an ion through an actual lung. At the same time the implementation is straightforward and the computational effort involved is manageable with current radiotherapy planning systems. Calculation times have been found to increase by a factor 3-10, depending on the circumstances.

The identification of the fractal tissue voxel may be performed by comparing the average density of the voxel to a selected threshold value. The threshold value may be set in dependence of experience or an expected value for tissue in the area of the patient. The threshold value may alternatively be related to the tissue surrounding the fractal tissue. For example, a voxel having an average density less than a selected threshold value, for example, 50% of the density of tissue surrounding the fractal tissue, or of tissue of an adjacent organ, may be identified as a fractal tissue voxel, for example, a lung tissue voxel.

The grid preferably has a lattice constant corresponding to the size of the cavities in the fractal tissue. For example, for lung tissue the lattice constant may correspond to the size of the alveoli in the lung volume to be treated, typically between 0.03 mm and 0.1 mm.

Preferably, the relationship between the volume of the second portion and the total volume of the cell corresponds to the relationship between alveoli and tissue in a lung. This value is typically between 5:1 and 4:1.

The size of the first portion and the size of the second portion are preferably selected such that the average density of the cell corresponds to the average density of lung, for example, between 0.2 and 0.3 g/cm3.

Preferably, the second voxel is inscribed in the grid at a different position from the first voxel and/or at an orientation of the grid relative to the second voxel that differs from the orientation of the first voxel in the grid.

The step of inscribing the voxel may comprise inscribing a volume comprising a number of adjacent voxels in the grid at one time, and the step of calculating the propagation of ions comprises calculating the propagation of ions through the volume.

The cells may be cubical or tetrahedral or display any other repeating structure The invention also relates to a computer program product comprising computer readable code which, when run in a computer, will cause the computer to perform the method as defined above, and to a computer system comprising a processor for executing computer programs and program memory, such as a non-transitory program memory holding such a computer program product. The invention also relates to a treatment planning system comprising a computer system for carrying out the method.

BRIEF DESCRIPTION OF THE DRAWINGS

The invention will be described in more detail in the following, by way of example and with reference to the appended drawings, in which.

DETAILED DESCRIPTION OF EMBODIMENTS

Figure 1:
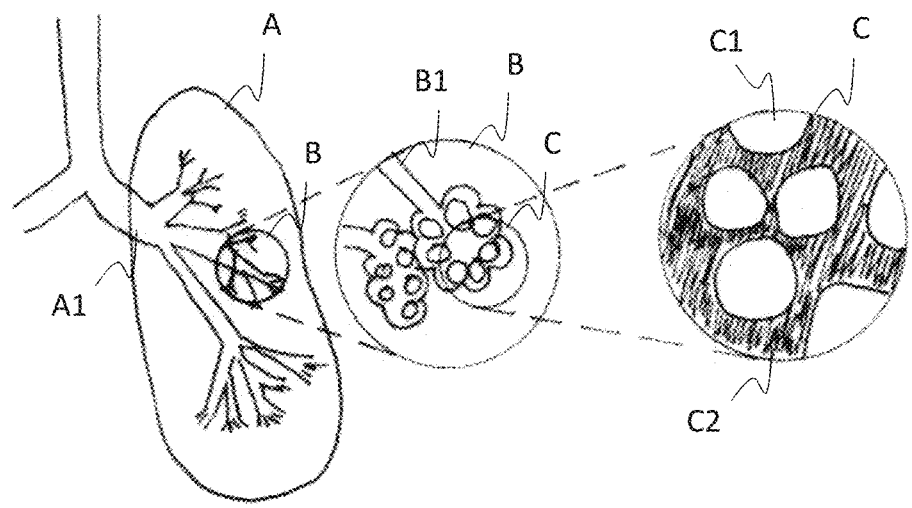
FIG. 1 shows the general structure of lung tissue.

FIG. 1 illustrates, on three levels A, B and C, the interior structure of a lung, which is well known to the skilled person. The area marked with an A depicts an overall lung portion with bronchi A1. The area marked with a B is an enlarged portion corresponding to the circle B in the area marked A, showing how the bronchi branch into bronchioles B1. The area marked with a C is a further enlargement corresponding to the circle C in the area marked B, showing that the bronchioles divide into microscopic air cavities known as alveoli C1. The alveoli C1 are surrounded by lung tissue C2. As can be seen, within the lung tissue C2 there are several alveoli C1, which cause a fractal structure in the lung tissue. The lung tissue C2 itself has a density of approximately 1, that is, close to water. The density in the air cavities C1 is close to zero. The average density in a lung is typically between 0.2 and 0.25 g/cm3, indicating that in total, approximately 75-80% of the lung is filled with air.

Figure 2:
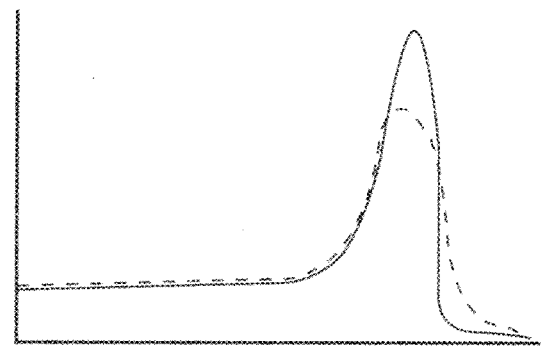
FIG. 2 shows a typical Bragg peak and one affected by the ions travelling through lung tissue.

FIG. 2 illustrates a typical Bragg peak resulting from ions travelling through homogenous tissue, shown as a solid line, and a typical Bragg peak resulting from ions travelling through lung tissue, shown as a dashed line. As can be seen, the second Bragg peak is wider and less precise, illustrating that the dose delivery will be broader in lung tissue.

Figure 3:
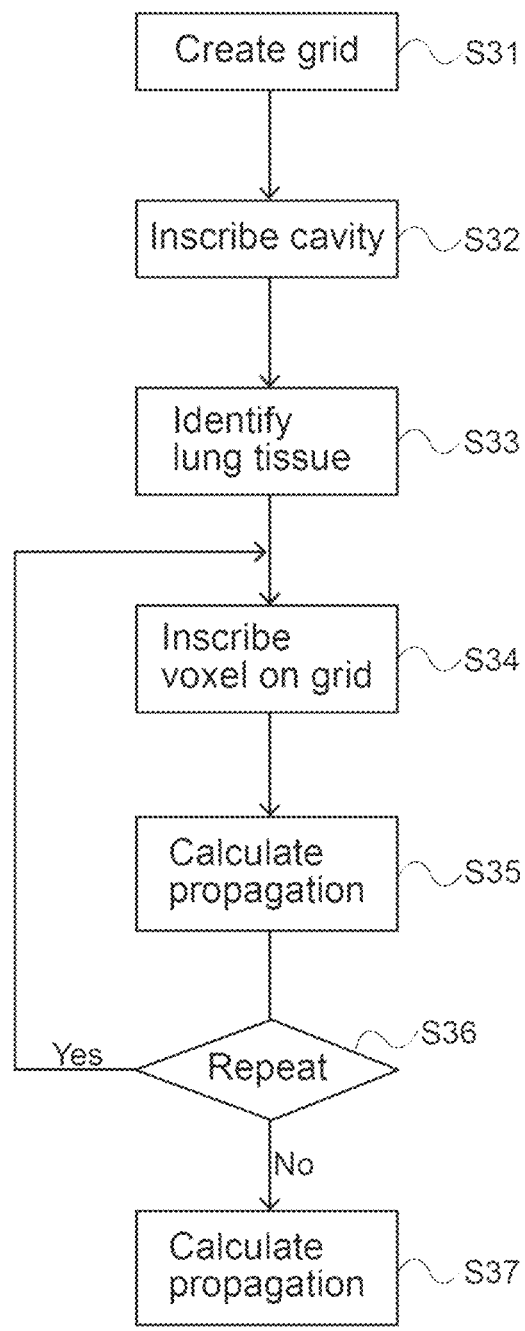
FIG. 3 is a flow chart outlining a method according to the invention.

FIG. 3 is a flow chart of a method according to a typical embodiment of the invention. In step S31, a regular matrix is created, forming a regular grid having a number of identical cells. The size of the grid is greater than the size of a voxel in the radiotherapy planning system, to allow a voxel to be inscribed within the grid. A typical voxel size is between 1 and 3 mm. The size of each cell corresponds to the approximate size of alveoli, typically between 0.03 and 0.1 mm.

In step S32, a cavity is inscribed in each cell, to emulate the presence of alveoli. The cavity may have any suitable geometrical form, for example spherical or ellipsoid. The size of the cavity corresponds to the approximate size of alveoli in the tissue concerned. In particular, the ratio within each cell of the volume of the cavity to the total volume of the cell should be close to the ratio of air to tissue in the lung.

In step S33, the dose voxels within the patient that consist of lung tissue are identified. This can be done by identifying as lung dose voxels the voxels having an average density representing a mixture of tissue and air, such as is typical for lungs.

The following steps are performed for each dose voxel that is identified in step S33 as a lung dose voxel.

In step S34, for each lung dose voxel, the voxel is inscribed inside the grid, so that the grid pattern of cavities will be superimposed on the voxel. Preferably this is done for one voxel at a time.

In step S35, the propagation of ions through the voxel is calculated, treating any portion of the voxel corresponding to a part of an air cavity as an air-filled cavity and any remaining portion as lung tissue. Step S36 indicates that the loop of steps S34 and S35 is performed a number of times, once for each dose voxel identified as a lung dose voxel.

For the voxels not identified as lung dose voxels, it can be assumed that they are heterogeneous and ion propagation may be calculated based on each voxel's average density as is well known in the art as indicated by step S37.

Figure 4A:
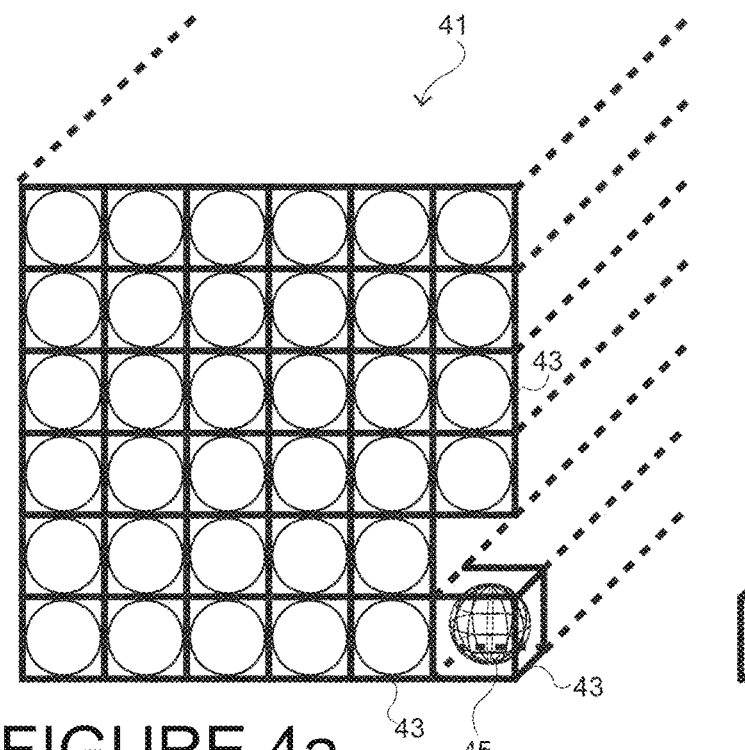
FIGS. 4a and 4b illustrate a first example of a grid that may be used in the method according to the invention.
Figure 5A:
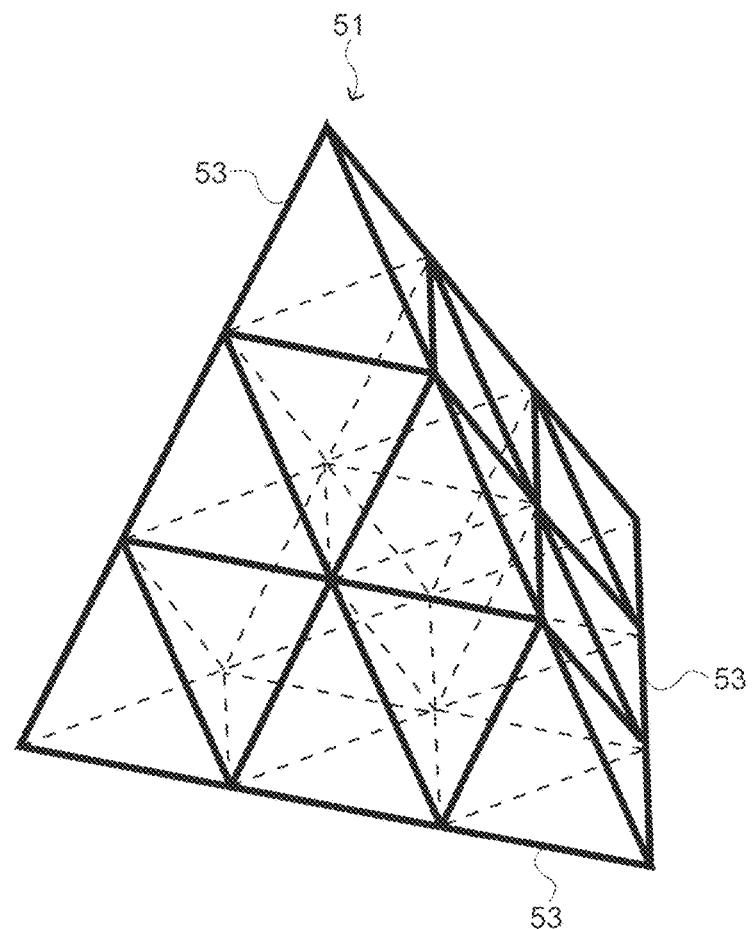
FIGS. 5a and 5b illustrate a second example of a grid that may be used in the method according to the invention.

In step S31, the grid can be any regular three-dimensional grid comprising a number of identical cells, for example a cubic structure made up of smaller cubes or a shape made up of tetrahedrons. Such examples are illustrated in FIGS. 4a and 5a.

In preferred embodiments, step S34 may be varied by changing the position of the voxel inside of the grid, and/or the orientation of the grid relative to the voxel. For example, the grid may be rotated freely, or by a certain angle around a certain axis. These changes may be applied randomly, or according to a suitable algorithm. As an alternative to inscribing one voxel at a time inside the grid, if a larger grid is used, a volume comprising a number of adjacent voxels may be inscribed inside the grid. Superimposing two regular structures on top of each other may, however, lead to interference effects which may distort the results.

As mentioned for step S32, the air cavities inscribed in the cells of the grids may have any suitable shape and size. A suitable choice will be a regular geometric shape that will fill approximately the same fraction of the volume of the cell as the fraction of the lung volume that is air filled. Typically in a lung, the alveoli constitute between 75 and 80% of the total volume, resulting in a density between 0.20 and 0.25 g/cm3. A sphere of radius r inscribed in a cube having a side length of 2 r fills approximately 77% of the cube, leaving 23% that will be considered tissue. Hence, the result of this will be a density of approximately 0.23 g/cm3, which is close to the actual density of lung tissue.

As the size and distribution of alveoli in lung tissue may vary between different portions of the same lung, it may be advantageous to vary the size of the air cavity relative to the whole cell, to obtain different average densities for different portions of the lung. This may even be varied for each dose voxel, to account for the actual density of the lung in each individual voxel.

Instead of calculating the propagation of ions in step S35, it would be possible to retrieve the value as the best possible match from a pre-calculated lookup table.

Figure 4B:
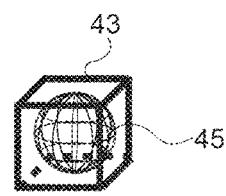

FIGS. 4a and 4b illustrate a first possible format for the grid to be used according to the invention. In this first format each grid cell has a cubic shape and inside each cell a sphere 43 is inscribed, representing an air cavity. FIG. 4a illustrates a side view of a grid 41 comprising 6×6 cells in one plane. As will be understood, although only indicated in FIG. 4a, the grid is three-dimensional and each cell is cubical, although in FIG. 4a only one cell is shown as cubical and the rest are just shown as squares. FIG. 4b is a 3D representation of one individual cell within the grid, as a cube with a sphere inscribed in it.

Figure 4C:
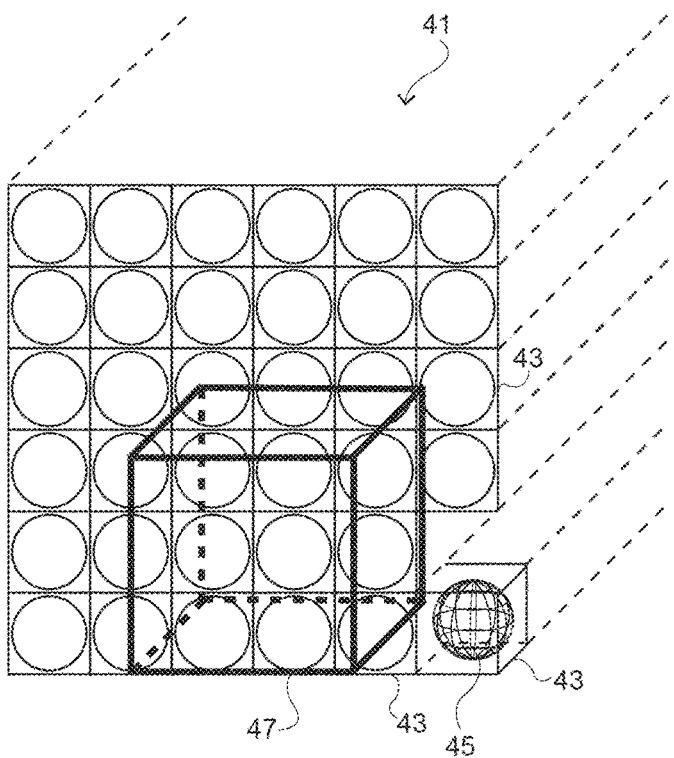
FIG. 4c illustrates a voxel inscribed in the grid.

FIG. 4c illustrates a voxel 47 inscribed in the grid 41. Normally the voxel 47 is much larger than each cell 43 of the grid and will overlap a number of cells. The position of the voxel 47 on the grid 41 may vary, and different restrictions may be set. For example, a criterion may be set that the voxel must overlap at least one cell fully. This means that the voxel can overlap perfectly with one cell, or with a complete number of cells in such a way that the edges of the voxel and the edges of the cell or cells coincide. Alternatively, the voxel may be inscribed so that it overlaps one cell completely and also extends into one or more of the surrounding cells. It is also possible to let a voxel extend into a number of cells without overlapping any of the cells completely.

Figure 5B:
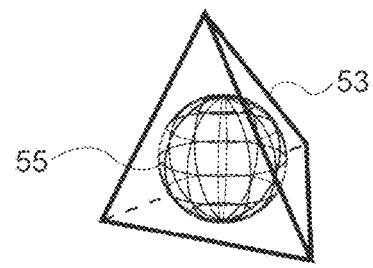

FIGS. 5a and 5b illustrate a second possible format for the grid to be used according to the invention in the shape of a tetrahedron 51. In this example, each grid cell 53 is shaped as a tetrahedron and inside each cell a geometric shape 55 is inscribed, although this is only indicated for some of the cells, for clarity of the Figure. To inscribe a dose voxel inside each tetrahedron-shaped cell 53, the tetrahedron is preferably discretized along its four principal axes and an alveoli is placed at the vertices.

As will be understood, the shape of the cell and the shape of the air cavity may be selected freely as long as the relationship between the air cavity and the total cell volume matches the actual fraction of alveoli within the corresponding portion of the lung.

As will be understood, the method is typically implemented as a computer program product, which may be stored on any type of storage medium and executed in a radiotherapy dose planning system used for ion radiotherapy planning.

Figure 6:
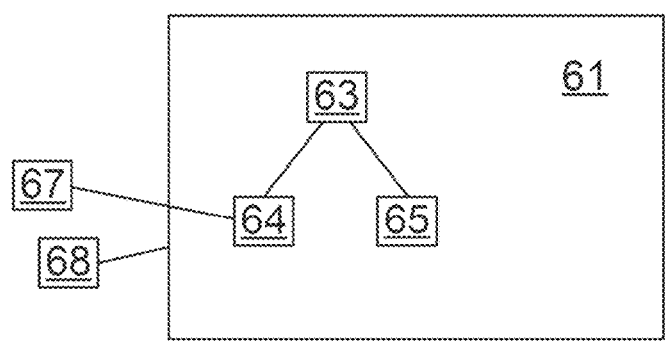
FIG. 6 is a schematic representation of a computer system in which the inventive method may be performed.

FIG. 6 is a schematic representation of a computer system in which the inventive method may be performed. A computer 61 comprises a processor 63, a data memory 64 and a program memory 65. Preferably, a user input means 67, 68 is also present, in the form of a keyboard, a mouse, a joystick, voice recognition means or any other available user input means. The user input means may also be arranged to receive data from an external memory unit.

The data memory 64 typically holds image data related to a patient that is to receive treatment, such as density information, as input data to the treatment planning.

If the values for ion propagation have been pre-calculated, the data memory 64 also holds these values, typically in the form of a lookup table. As will be understood, the data memory 64 is only shown schematically. There may be several data memory units, each holding one or more different types of data, for example, one data memory for patient data, one for the ion propagation values, etc.

The program memory 65 comprises a computer program arranged to run in the processor 63 to make the system perform the method according to the invention.

The invention claimed is:

1. A method of performing dose calculations for ion radiotherapy of a volume to be treated, said volume comprising a plurality of voxels, comprising the steps of:
   a. identifying, in the volume to be treated, at least one voxel of the plurality of voxels as a fractal tissue voxel representing tissue having an average density comprising a mixture of tissue and air;
   b. inscribing the identified at least one voxel in a three-dimensional grid comprising a plurality of cells such that a grid pattern is configured to be superimposed on the identified at least one voxel,
   c. wherein each cell of the three-dimensional grid comprises: a first portion representing a first density corresponding to a density of a tissue and a second portion representing a second density corresponding to a density of air, the first and second portions forming a cell pattern; and
   d. calculating a propagation of ions through the identified at least one voxel based on the cell pattern in at least one cell of the three-dimensional grid with which the identified at least one voxel overlaps.

2. The method according to claim 1, wherein the identified at least one voxel has an average density less than a selected threshold value of 50% of a density of a tissue surrounding the identified at least one voxel.

3. The method according to claim 1, wherein the grid has a lattice constant corresponding to a size of alveoli in the volume to be treated of a lung, between 0.03 mm and 0.1 mm.

4. The method according to claim 1, wherein a relationship between a volume of the second portion and a total volume of the first and second portions of the at least one cell of the three-dimensional grid corresponds to a relationship between alveoli and tissue in a lung.

5. The method according to claim 1, wherein a relationship between a volume of the second portion and a total volume of the first and second portions of the at least one cell of the three-dimensional grid is between 5:1 and 4:1.

6. The method according to claim 1, wherein a size of the first portion and a size of the second portion are selected such that the average density of the at least one cell of the three-dimensional grid corresponds to an average density of lung tissue between 0.2 and 0.3 g/cm3.

7. The method according to claim 1, further comprising the step of inscribing a second voxel in the grid at a different position from the identified at least one voxel.

8. The method according to claim 1, further comprising the step of inscribing a second voxel in the grid at an orientation of the grid relative to the second voxel that differs from an orientation of the grid relative to the identified at least one voxel.

9. The method according to claim 1, comprising: inscribing a volume comprising a plurality of adjacent voxels that are adjacent to the identified at least one voxel in the grid at one time; and calculating the propagation of ions through the volume comprising the adjacent voxels.

10. The method according to claim 1, wherein the cells of the three-dimensional grid are cubical or tetrahedrical.

11. A non-transitory computer readable medium storing a computer program product comprising computer readable code which, when run in a computer, is configured to cause the computer to perform the method according to claim 1.

12. A computer system comprising a processor for executing computer programs and the non-transitory computer readable medium storing the computer program product according to claim 11.

13. A treatment planning system for calculating radiation therapy treatment plans, comprising a computer system according to claim 12.

* * * * *